United States Patent

Noguchi et al.

[11] Patent Number: 6,022,713
[45] Date of Patent: Feb. 8, 2000

[54] PROCESS FOR PRODUCING NUCLEOSIDE 5'-TRIPHOSPHATES AND APPLICATION OF THE SAME

[75] Inventors: Toshitada Noguchi, Choshi; Toshikazu Shiba, Sapporo, both of Japan

[73] Assignee: Yamasa Corporation, Chiba, Japan

[21] Appl. No.: 09/101,683

[22] PCT Filed: Nov. 14, 1997

[86] PCT No.: PCT/JP97/04159

§ 371 Date: Jul. 15, 1998

§ 102(e) Date: Jul. 15, 1998

[87] PCT Pub. No.: WO98/22614

PCT Pub. Date: May 28, 1998

[30] Foreign Application Priority Data

Nov. 19, 1996 [JP] Japan ................................. 8-323488
Dec. 4, 1996 [JP] Japan ................................. 8-339055
Apr. 30, 1997 [JP] Japan ................................. 9-100908

[51] Int. Cl.[7] ............................ C12P 19/30; C12P 19/26; C12P 19/00; C12P 19/18
[52] U.S. Cl. ................................ 435/89; 435/84; 435/72; 435/97
[58] Field of Search ..................... 435/89, 84, 72, 435/97

[56] References Cited

U.S. PATENT DOCUMENTS 5,409,817  4/1995  Ito et al. ................................... 435/74
5,516,665  5/1996  Wong ........................................ 435/97

OTHER PUBLICATIONS

Akio Kuroda and Arthur Kornberg, Polyphosphate kinase as a nucleoside diphosphate kinase in *Escherichia coli* and *Pseudomonas aeruginosa*, Proc. Natl. Acad. Scie. USA vol. 94, pp. 439–442 (Jan., 1997).

Chi–Huey Wong, et al., Practical synthesis of carbohydrates based on aldolases and glycosyl transferases, Pure Appl. Chem. vol. 65 No. (4), pp. 803–808 (1993).

*Primary Examiner*—Francisco Prats
*Attorney, Agent, or Firm*—Wenderoth, Lind & Ponack, L.L.P.

[57] ABSTRACT

The present invention relates to a process for producing nucleoside 5'-triphosphates (NTP) from nucleoside 5'-diphosphates (NDP) other than adenosine 5'-diphosphate (ADP), characterized by using a polyphosphate kinase as an enzyme and polyphosphate as the phosphate donor; and application of this process to various glycosylation reactions.

This process makes it possible to conveniently and economically synthesize NTP from NDP enzymatically. Also, it becomes possible thereby to economically recycle and synthesize sugar nucleotides and synthesize, for example, oligosaccharides associating therewith without resort to expensive phosphoenol pyruvate, ATP, etc. in the reactions for reproducing or converting NDP into NTP in the systems for enzymatically synthesizing oligosaccharides by combining, for example, with the synthesis of sugar nucleotides.

7 Claims, 12 Drawing Sheets

6,022,713

SEQUENCE LISTING

<160> NUMBER OF SEQ ID NOS: 6

<210> SEQ ID NO 1
<211> LENGTH: 24
<212> TYPE: DNA
<213> ORGANISM: Primer

<400> SEQUENCE: 1
taccatgggt caggaaaagc tata                                    24

-continued

```
<210> SEQ ID NO 2
<211> LENGTH: 29
<212> TYPE: DNA
<213> ORGANISM: Primer

<400> SEQUENCE: 2
atggatcctt attcaggttg ttcgagtga                                    29

<210> SEQ ID NO 3
<211> LENGTH: 29
<212> TYPE: DNA
<213> ORGANISM: Primer

<400> SEQUENCE: 3
gcgaattctg atatactggg atgcgatac                                    29

<210> SEQ ID NO 4
<211> LENGTH: 27
<212> TYPE: DNA
<213> ORGANISM: Primer

<400> SEQUENCE: 4
acgtcgacac cgatacggat gtatctt                                      27

<210> SEQ ID NO 5
<211> LENGTH: 27
<212> TYPE: DNA
<213> ORGANISM: Primer

<400> SEQUENCE: 5
tagaattcat accataagcc taatgga                                      27

<210> SEQ ID NO 6
<211> LENGTH: 27
<212> TYPE: DNA
<213> ORGANISM: Primer

<400> SEQUENCE: 6
taggatcctt aatcgggata tccctgt                                      27
```

PROCESS FOR PRODUCING NUCLEOSIDE 5'-TRIPHOSPHATES AND APPLICATION OF THE SAME

BACKGROUND OF THE INVENTION

1. Field of the Invention

The present invention relates to a process for the production, or regeneration, of nucleoside 5'-triphosphate (NTPs) from nucleoside 5'-diphosphates (NDPs) other than adenosine 5'-diphosphate (ADP), and to applications of the process to, for example, the synthesis of oligosaccharides.

2. Description of the Related Art

Development of the nucleic acid industry, in forms such as nucleic acid fermentation or enzymatic degradation of nucleic acid, has enabled low cost manufacture of nucleosides and nucleoside 5'-monophosphates (NMPs), some of which are produced and sold as pharmaceuticals or as raw materials for pharmaceuticals. Also, development of pharmaceuticals making use of nucleosides, nucleotides, and their derivatives has been actively performed. Moreover, recent advancement of sugar chain engineering entails active studies of synthesis of sugar nucleotides, which serve as substrates in enzymatic synthesis of oligosaccharides.

Thus, in contrast to the case of NMPs, which are manufactured and supplied economically, no economical manufacturing method for NTPs, led by adenosine 5'-triphosphate, has so far been established, although there have been known a number of synthesis methods, including chemical synthesis methods and methods making use of a microorganism or an enzyme, and therefore, NTPs currently available on the market are quite expensive.

Recently, many studies have been conducted to develop techniques for the synthesis of oligosaccharides by use of glycosyltransferase and making use of sugar nucleotide as a substrate. Of such studies, a sugar nucleotide recycling method proposed by Scripps Research Institute in the U.S.A. has become of interest (PCT Kohyo Publication No. 7-500248 and JP-A No. 7-79792). This method employs NTP and sugar 1-phosphate as substrates and also uses sugar nucleotide pyrophosphorylase and glycosyltransferase, to thereby synthesize a sugar nucleotide, and simultaneously, while the resultant sugar nucleotide is used as a monosaccharide donor, glycosyltransfer reaction is performed efficiently, to thereby synthesize an oligosaccharide. This method is characterized in that the NDP produced from the glycosyltransfer reaction is regenerated as NTP by the mediation of a combination of phosphoenolpyruvic acid and pyruvate kinase, so that the NTP is reused as a substrate for the synthesis of sugar nucleotide, to thereby reduce the amount of expensive NTP and make the glycosyltransfer reaction efficient, resulting in an expected reduction in costs for the manufacture of oligosaccharides.

The above-mentioned recycling method, though advantageous in that it does not use a large amount of expensive NTP, requires a large amount of expensive phosphoenolpyruvic acid for regenerating NTP. Therefore, this method is not necessarily satisfactory in practice.

In the conversion reaction from NDP to NTP, other enzymes, e.g., nucleoside-diphosphate kinase, may be used in place of pyruvate kinase. However, in this case also, expensive adenosine 5'-triphosphate (ATP) is required as a phosphate donor, and therefore, such a replacement does not effect a radical resolution.

Accordingly, the present invention is directed to a more practical method for the synthesis, or regeneration, of NTP from NDP without use of expensive phosphoenolpyruvic acid or ATP, and also to applications of the method in, for example, the synthesis of oligosaccharides.

The present inventors have conducted careful studies in an attempt to attain the above object, and have found that conventionally known polyphosphate kinase (Biochim. biophys. Acta., 26, 294–300 (1957)) is endowed with activity capable of phosphorylating NDPs other than ADP, through use of polyphosphate as a phosphate donor, to thereby synthesize NTPs. The inventors have extended their studies toward applications of this method to the synthesis of oligosaccharides, and as a result, they were able to confirm that the method is more practical than the aforementioned sugar nucleotide recycling method. The present invention was accomplished based on these findings.

SUMMARY OF THE INVENTION

Accordingly, the present invention provides a process for the production of NTPs from NDPs other than ADP, characterized in that polyphosphate kinase is used as an enzyme, and polyphosphate is used as a phosphate donor.

The present invention also provides a process for the regeneration of NTPs from NDPs other than ADP that have been produced through another enzymatic process, characterized in that polyphosphate kinase is used as an enzyme, and polyphosphate is used as a phosphate donor.

Moreover, the present invention provides a process for the production of glycosylated compounds of acceptor sugars, wherein while glycosylated compounds of acceptor sugars are produced from sugar nucleotides and acceptor sugars by the mediation of glycosyltransferase, NMPs or NDPs which are produced therefrom are transformed to NTPs then to sugar nucleotides, to thereby achieve recycling of the NMPs or NDPs, characterized in that the transformation from NDPs to NTPs is performed through use of polyphosphate kinase as an enzyme, and polyphosphate as a phosphate donor.

DESCRIPTION OF THE PREFERRED EMBODIMENT

Figure 1:
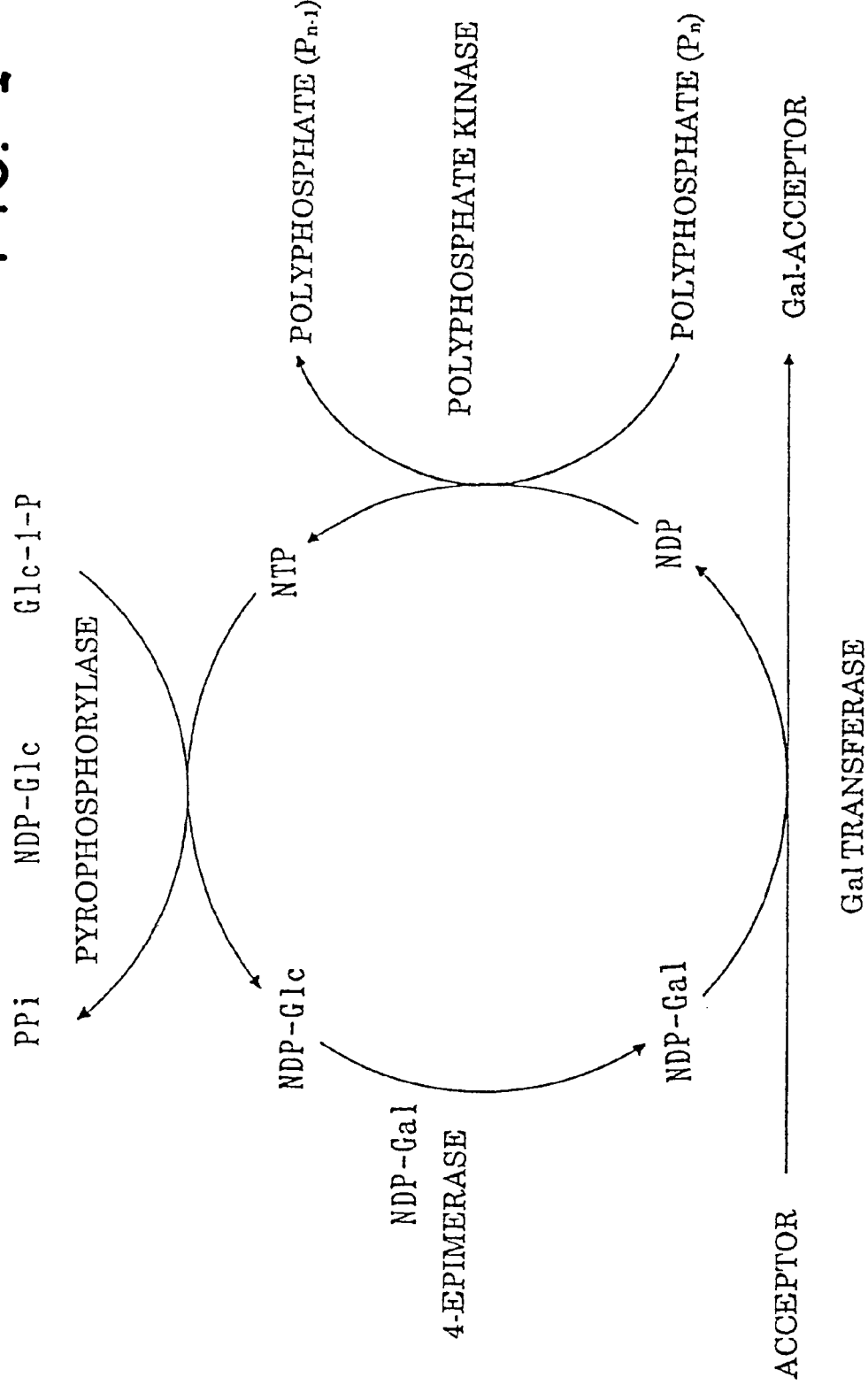
FIGS. 1 and 2 show the reaction schemes for the manufacture of a galactosylated compound of an acceptor sugar.

The present invention is unique in that NTP is produced from NDP by use of polyphosphate kinase as an enzyme and polyphosphate as a phosphate donor. Examples of nucleosides that constitute NDP and NTP include guanosine, inosine, xanthosine, cytidine, uridine, and ribothymidine.

No particular limitation is imposed on the type of polyphosphate kinase used in the present invention so long as it is categorized as a polyphosphate kinase (E.C. 2.7.4.1.) having activity capable of synthesizing NTP through phosphorylation of NDP; and animal-derived, plant-derived, or microorganism-derived polyphosphate kinase may be used. Of these, microorganism-derived, inter alia, *Escherichia coli*-derived, polyphosphate kinase is preferably used in view of, for example, ease of preparation of the enzyme. Alternatively, polyphosphate kinase may be prepared through cloning of a polyphosphate kinase gene by use of recent genetic engineering, to thereby mass-produce polyphosphate kinase from the resultant recombinant in a host such as *Escherichia coli* (*J. Biol. Chem.*, 267, 22556–22561 (1992)).

The polyphosphate kinase to be added to the reaction system may take any form so long as the enzyme exhibits the above-described activity. Specific examples of polyphosphate kinase include cells of a microorganism, a treated product of the cells, or an enzyme preparation obtained from the treated product.

Cells of a microorganism may be prepared by cultivating the microorganism through a customary process in a culture medium which permits growth of the microorganism, and then collecting cells by centrifugal separation, etc. For example, in the case of a bacterium which belongs to the genus *Bacillus* or *Escherichia coli*, the culture medium may be a bouillon medium, LB medium (1% trypton, 0.5% yeast extract, 1% common salt), or 2×YT medium (1.6% trypton, 1% yeast extract, 0.5% common salt). Cells of the microorganism having polyphosphate kinase activity may be prepared by inoculating seed cells to the medium, incubating at 30–50° C. for approximately 10–50 hours with optional stirring, and collecting cells by centrifugal separation of the obtained culture solution.

Examples of the treated product of cells of a microorganism include a destructed product or a cell-wall-denatured or cell-membrane-denatured product of cells obtained through treatment of the above-described cells of a microorganism by use of a typical method such as mechanical destruction (by a Waring blender, a French press, a homogenizer, a mortar, etc.), freeze-thawing, self-digestion, drying (freeze-drying, air-drying, etc.), enzyme-treatment (e.g., lysozyme), ultrasonic treatment, or chemical treatment (acid-treatment, alkali-treatment, etc.).

Examples of the enzyme preparation include a crude enzyme or a purified enzyme obtained through treatment of the above-described cells of a microorganism by a typical enzyme purification method (salting-out, precipitation at an isoelectric point, precipitation with an organic solvent, dialysis, chromatographic methods, etc.).

NDP to be added to a reaction mixture may be any type of NDP available on the market. The concentration of NDP in use is suitably determined within the range of 1–200 mM, preferably 10–100 mM. Commercially available polyphosphate may also be used as polyphosphate to be added to the reaction mixture. The concentration of polyphosphate in use is determined within the range of 1–1000 mM, preferably 10–200 mM when reduced as inorganic phosphate.

Conversion of NDP to NTP may be performed as follows. NDP and polyphosphate are added to a suitable buffer having a pH of 4–9. Subsequently, polyphosphate kinase is added in an amount of 0.001 units/ml or more, preferably 0.001–1.0 units/ml. The resultant mixture is allowed to react at 30° C. or higher, preferably at 32–37° C., for approximately 1–50 hours with optional stirring.

Regeneration of NTP from NDP that has been produced in another enzymatic reaction is performed in a similar manner except that NDP is added under the above-described reaction conditions.

The thus-synthesized or thus-regenerated NTP may optionally be separated and purified through a customary method for separation and purification of nucleotides (ion-exchange column chromatography, adsorption chromatography, salting-out, etc.). Also, NTP is effectively utilized as a substrate in the below-described system including, for example, a sugar nucleotide synthesis enzyme, and may be applied for the synthesis of oligosaccharides.

Briefly, there can be established a practical synthesis system for a glycosylated compound of an acceptor sugar, in which, while manufacturing a glycosylated compound of an acceptor sugar from a sugar nucleotide and the acceptor sugar by use of glycosyltransferase, NMP or NDP produced therefrom is converted to NTP, then to sugar nucleotide for recycling, through use of polyphosphate kinase as an enzyme and polyphosphate as a phosphate donor.

This synthesis system is characterized in that a glycosyl residue of the sugar nucleotide is transferred to the acceptor sugar by use of glycosyltransferase to form the glycosylated compound of the acceptor sugar and that NMP or NDP generated from the transfer reaction is regenerated as NTP for subsequent use, by use of polyphosphate and polyphosphate kinase.

In other words, the synthesis system is characterized by the co-existence of a reaction system in which a glycosyl residue of the sugar nucleotide is transferred to the acceptor sugar by use of glycosyltransferase to form the glycosylated compound of the acceptor sugar and a reaction system in which NMP or NDP formed in the transfer reaction is regenerated to NTP by use of polyphosphate and polyphosphate kinase.

Examples of glycosyltransferases which may be used in the synthesis system include galactosyltransferase, glucosyltransferase, fucosyltransferase, mannosyltransferase, glucuronyltransferase, sialyltransferase, N-acetylgalactosaminyltransferase, and N-acetylglucosaminyl transferase.

Accordingly, example glycosylated compounds of an acceptor sugar include an acceptor sugar adduct with galactose, glucose, fucose, mannose, glucuronic acid, sialyic acid, N-acetylgalactosamine, or N-acetylglucosamine.

No particular limitation is imposed on the acceptor sugar so long as it is a compound having a sugar chain which the above-described glycosyltransferases can recognize as a substrate. Examples include monosacchharides, oligosaccharides, polysaccharides, glycoproteins, and glycolipids. The sugar constituting these acceptor is not limited to ordinary sugar and may encompass deoxy saccharides, amino acids, uronic acids, saccharides, and sugar alcohols.

In the above-described synthesis system, conversion of NTP to sugar nucleotide is performed by causing NDP-glycosyl pyrophosphorylase and sugar 1-phosphate to react with NTP. When the sugar nucleotide obtained in the reaction has a glycosyl residue different from a glycosyl residue of interest, the sugar nucleotide may be converted to the desired one through reaction of epimerase, dehydrogenase, synthetase, etc.

The above-described synthesis system has such wide applicability that it is not limited to the above-described examples. The substrate and the enzyme which are the elements of the above-described synthesis system may be selected from known components in accordance with the target glycosylated product.

Combinations of specific elements of the above-described synthesis system have already been reported (see Japanese Patent Application Laid-Open (Kokai) No. 7–79792, PCT Kohyo Publication Nos. 6-505638, 7-500248, and 8-509619, and U.S. Pat. No. 5,409,817), and descriptions of these references are incorporated herein by reference. However, in the previously known reports, only a combination of acetylphosphate and acetate kinase and a combination of phosphoenol pyruvate and pyruvate kinase are described as a combination of a phosphate donor and a kinase. In contrast, the present invention employs polyphosphate as a phosphate donor and polyphosphate kinase as a kinase.

Application examples of the above-described synthesis system will next be shown.

Figure 2:
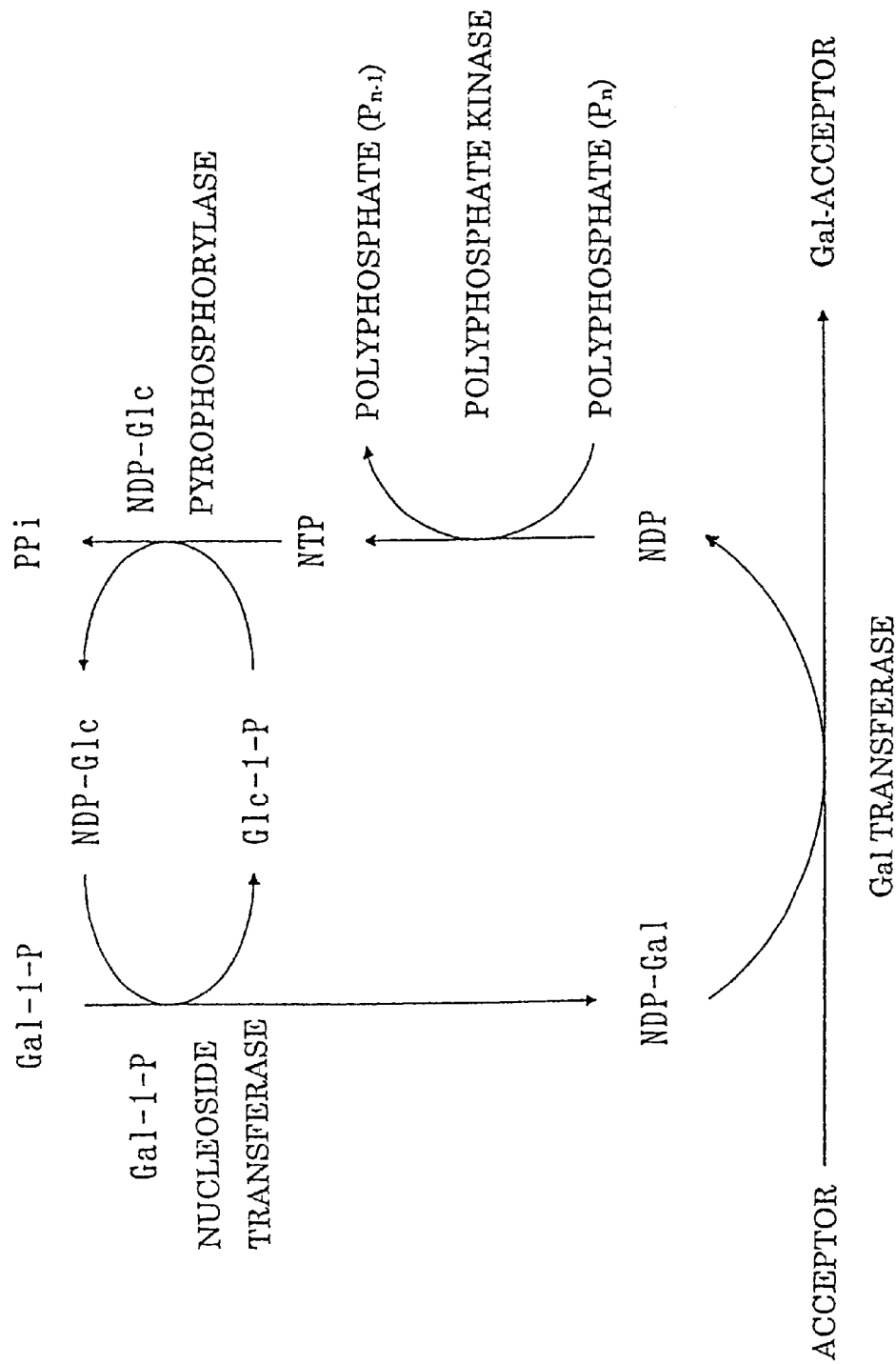

(1) A method for the manufacture of a galactosylated compound of an acceptor sugar, in which the galactosylated compound of an acceptor sugar is produced from a sugar nucleotide and the acceptor sugar by use of galactosyltransferase, and NDP formed in the reaction is transformed to NTP and then to a sugar nucleotide for recycling (FIGS. 1 and 2).

Figure 3:
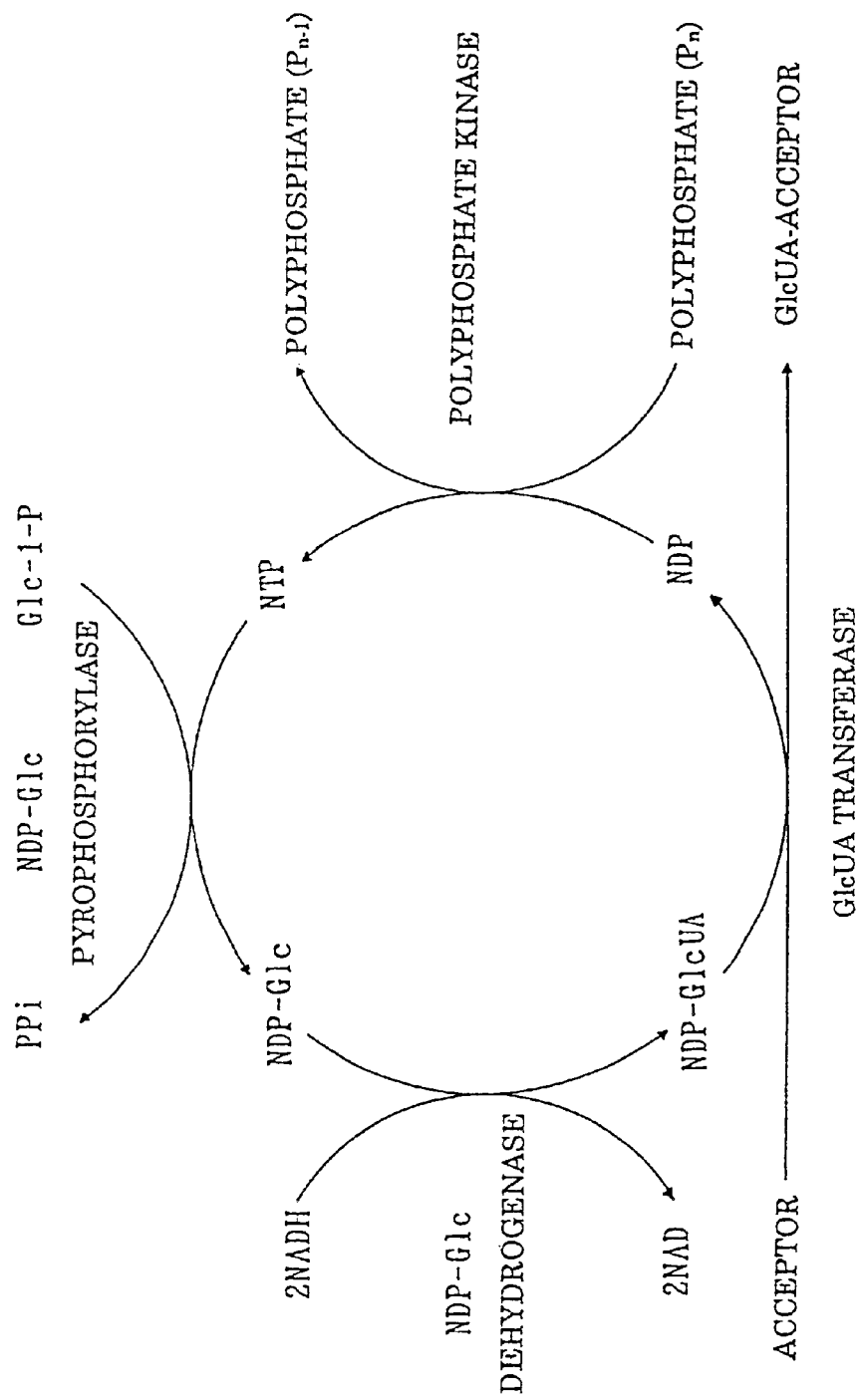
FIG. 3 shows the reaction scheme for the manufacture of a glucuronylated compound of an acceptor sugar.

(2) A method for the manufacture of a glucuronylated compound of an acceptor sugar, in which the glucuronylated compound of an acceptor sugar is produced from a sugar nucleotide and the acceptor sugar by use of glucuronyltransferase, and NDP formed in the reaction is transformed to NTP and then to a sugar nucleotide for recycling (FIG. 3).

Figure 4:
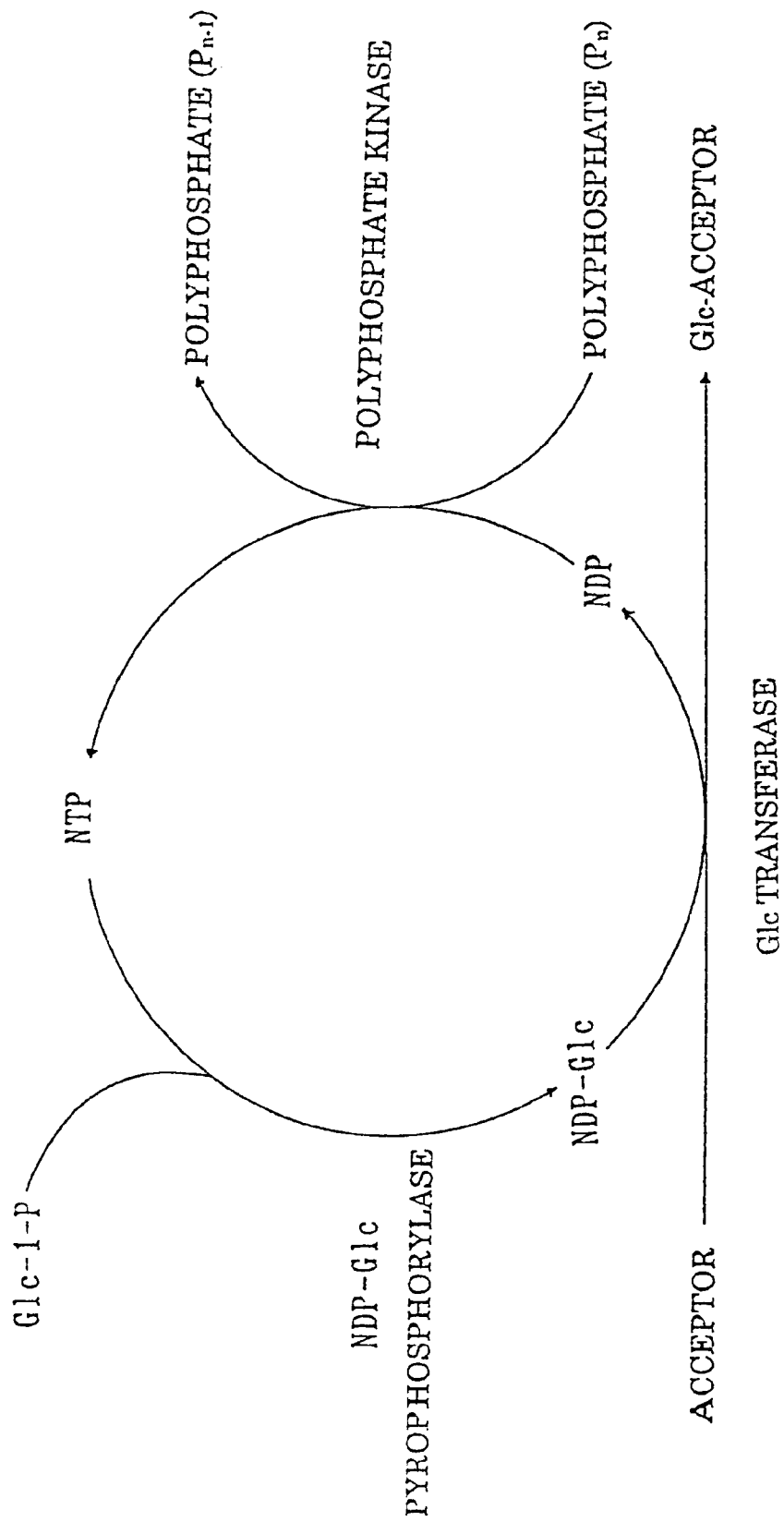
FIG. 4 shows the reaction scheme for the manufacture of a glucosylated compound of an acceptor sugar.

(3) A method for the manufacture of a glucosylated compound of an acceptor sugar, in which the glucosylated compound of an acceptor sugar is produced from a sugar nucleotide and the acceptor sugar by use of glucosyltransferase, and NDP formed in the reaction is transformed to NTP and then to a sugar nucleotide for recycling (FIG. 4).

Figure 5:
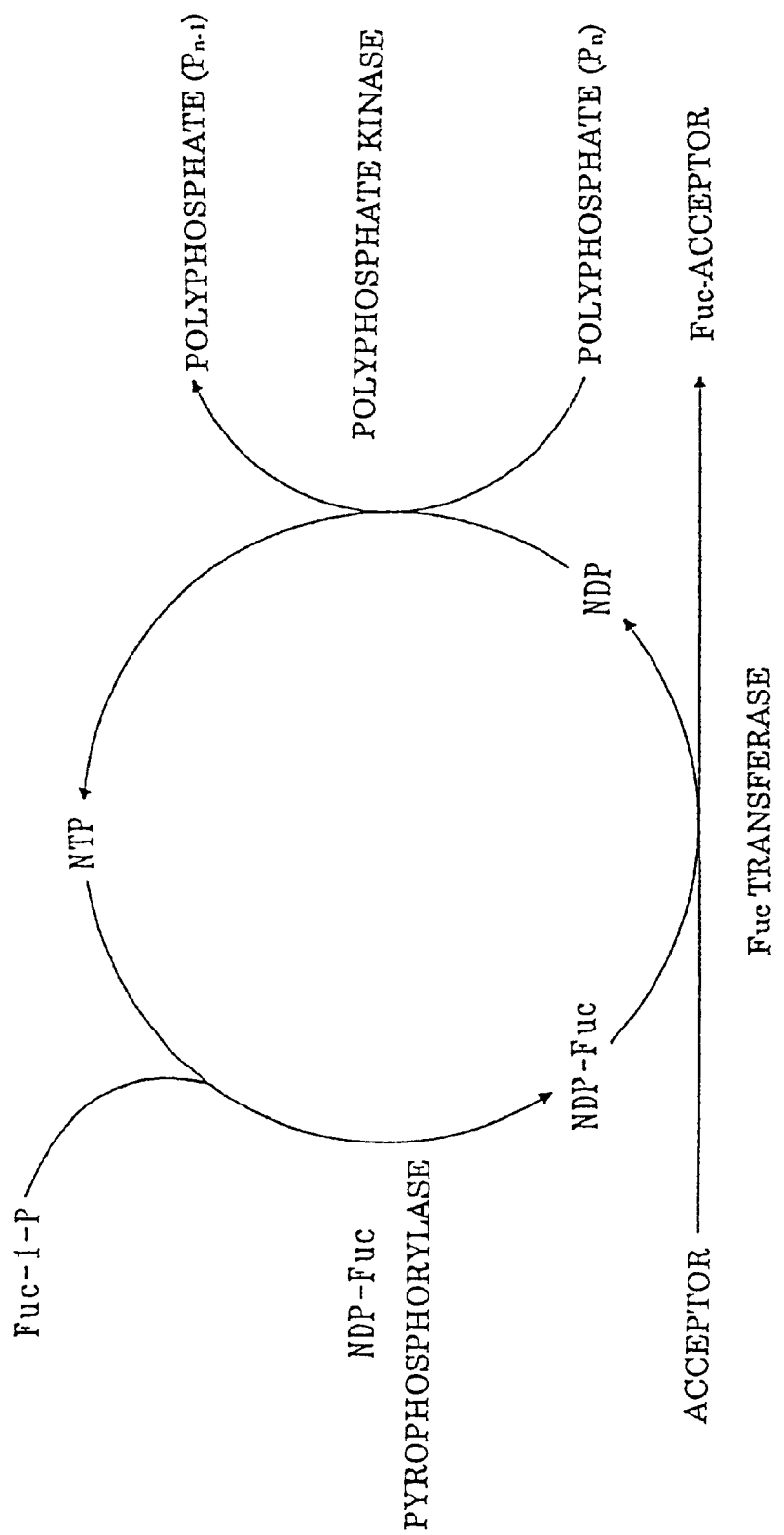
FIGS. 5 and 6 show the reaction schemes for the manufacture of a fucosylated compound of an acceptor sugar.
Figure 6:
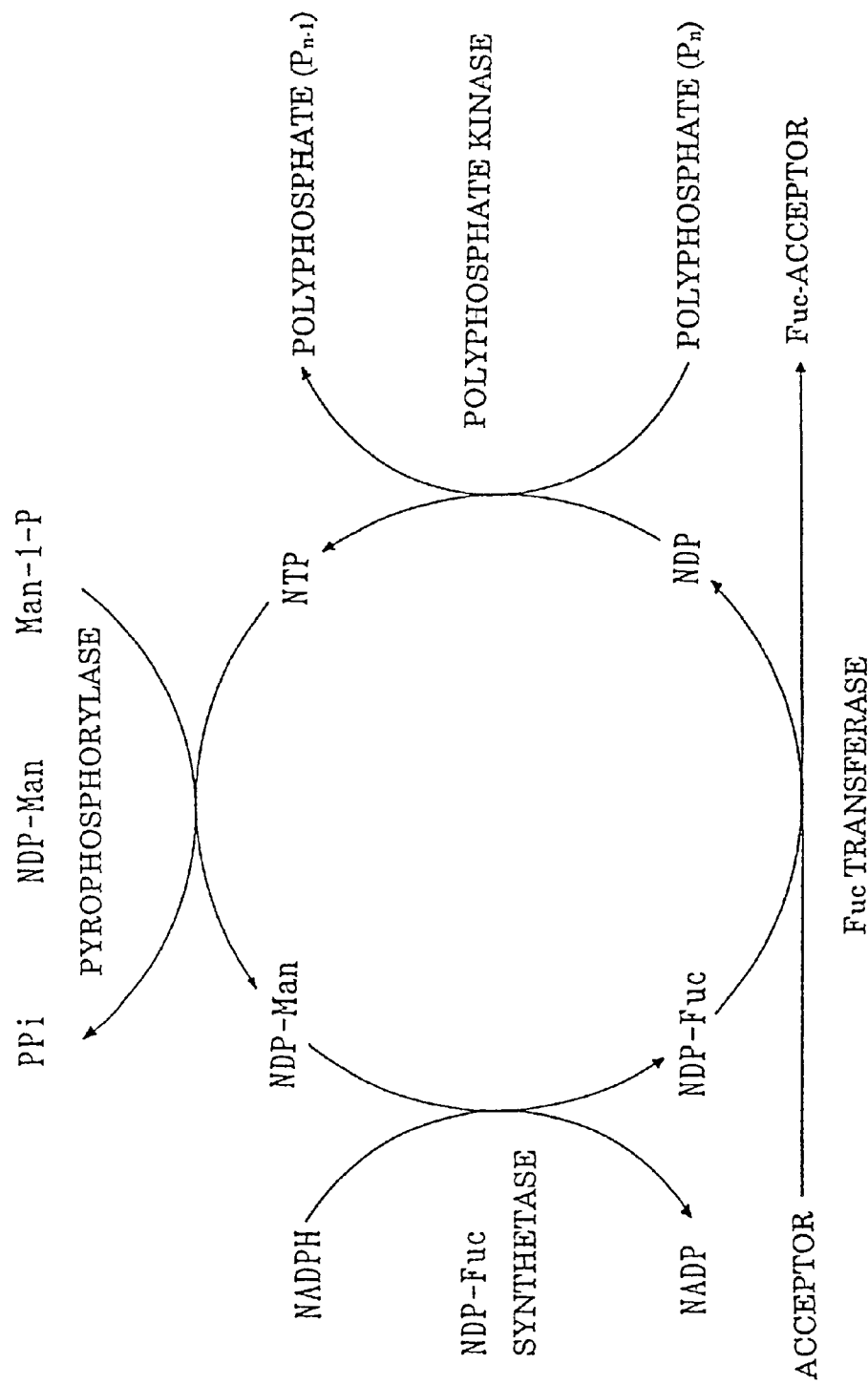

(4) A method for the manufacture of a fucosylated compound of an acceptor sugar, in which the fucosylated compound of an acceptor sugar is produced from a sugar nucleotide and the acceptor sugar by use of fucosyltransferase, and NDP formed in the reaction is transformed to NTP and then to a sugar nucleotide for recycling (FIGS. 5 and 6).

Figure 7:
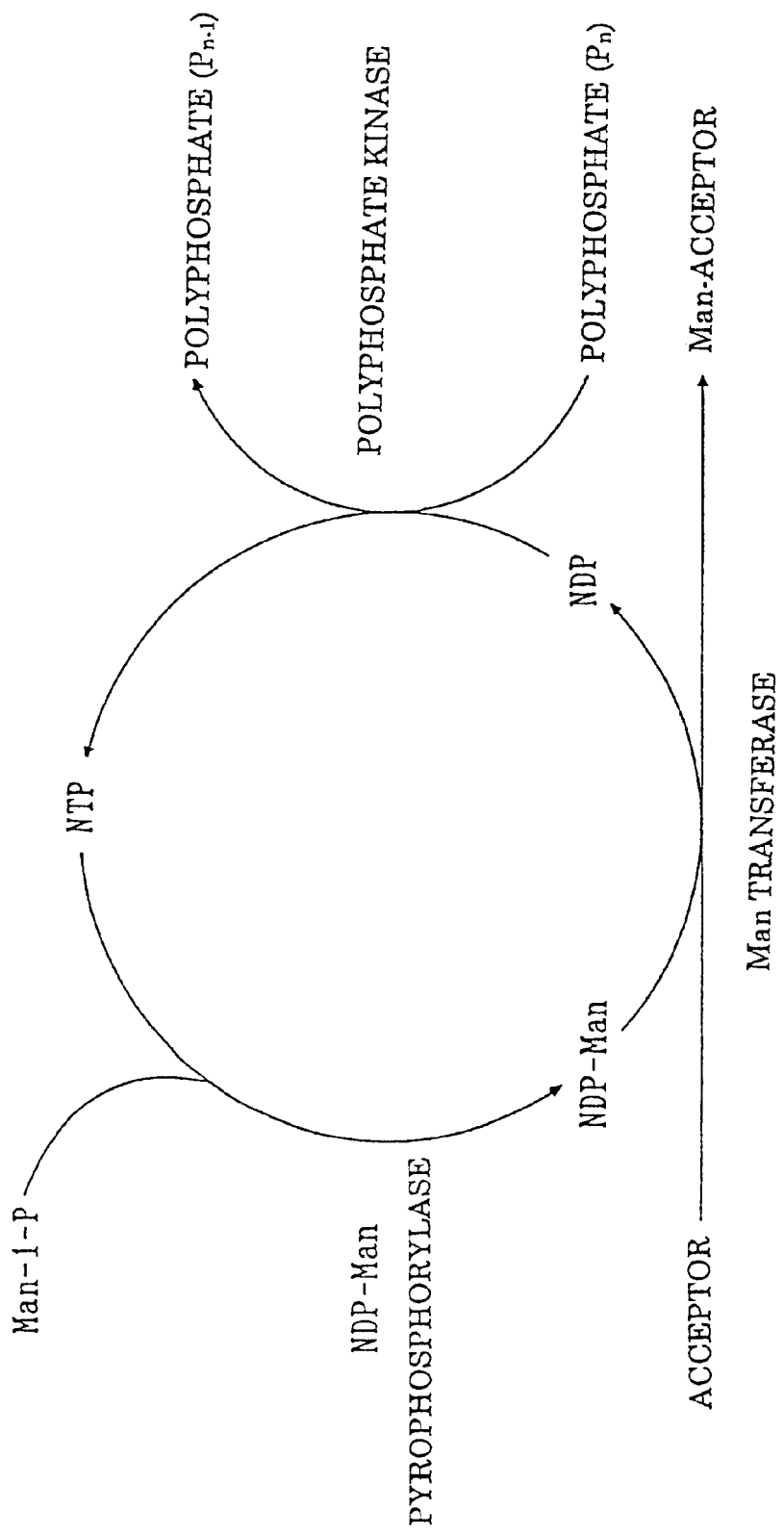
FIG. 7 shows the reaction scheme for the manufacture of a mannosylated compound of an acceptor sugar.

(5) A method for the manufacture of a mannosylated compound of an acceptor sugar, in which the mannosylated compound of an acceptor sugar is produced from a sugar nucleotide and the acceptor sugar by use of mannosyltransferase, and NDP formed in the reaction is transformed to NTP and then to a sugar nucleotide for recycling (FIG. 7).

Figure 8:
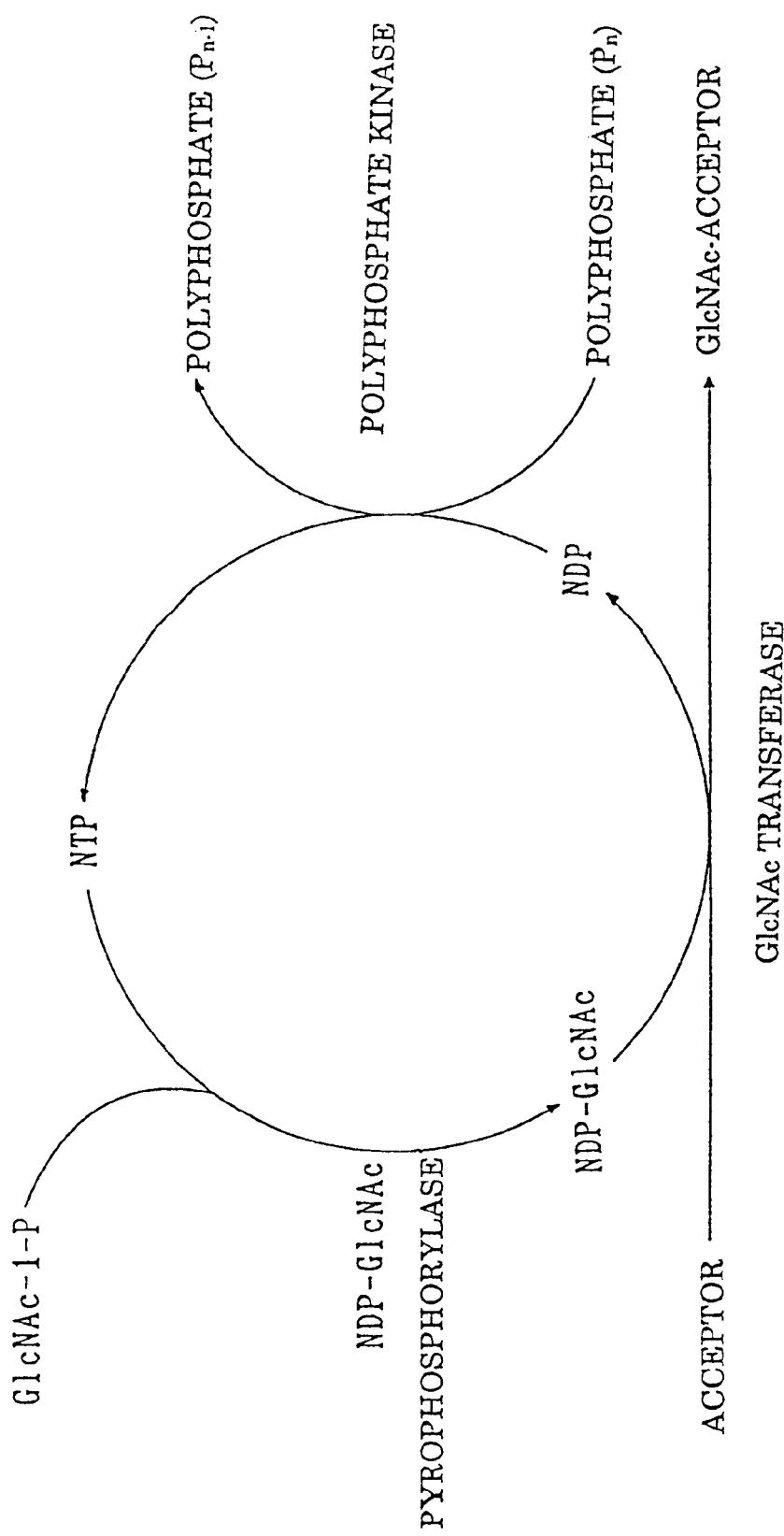
FIG. 8 shows the reaction scheme for the manufacture of an N-acetylglucosaminylated compound of an acceptor sugar.

(6) A method for the manufacture of an N-acetylglucosaminylated compound of an acceptor sugar, in which the N-acetylglucosaminylated compound of an acceptor sugar is produced from a sugar nucleotide and the acceptor sugar by use of N-acetylglucosaminyl transferase, and NDP formed in the reaction is transformed to NTP and then to a sugar nucleotide for recycling (FIG. 8).

Figure 9:
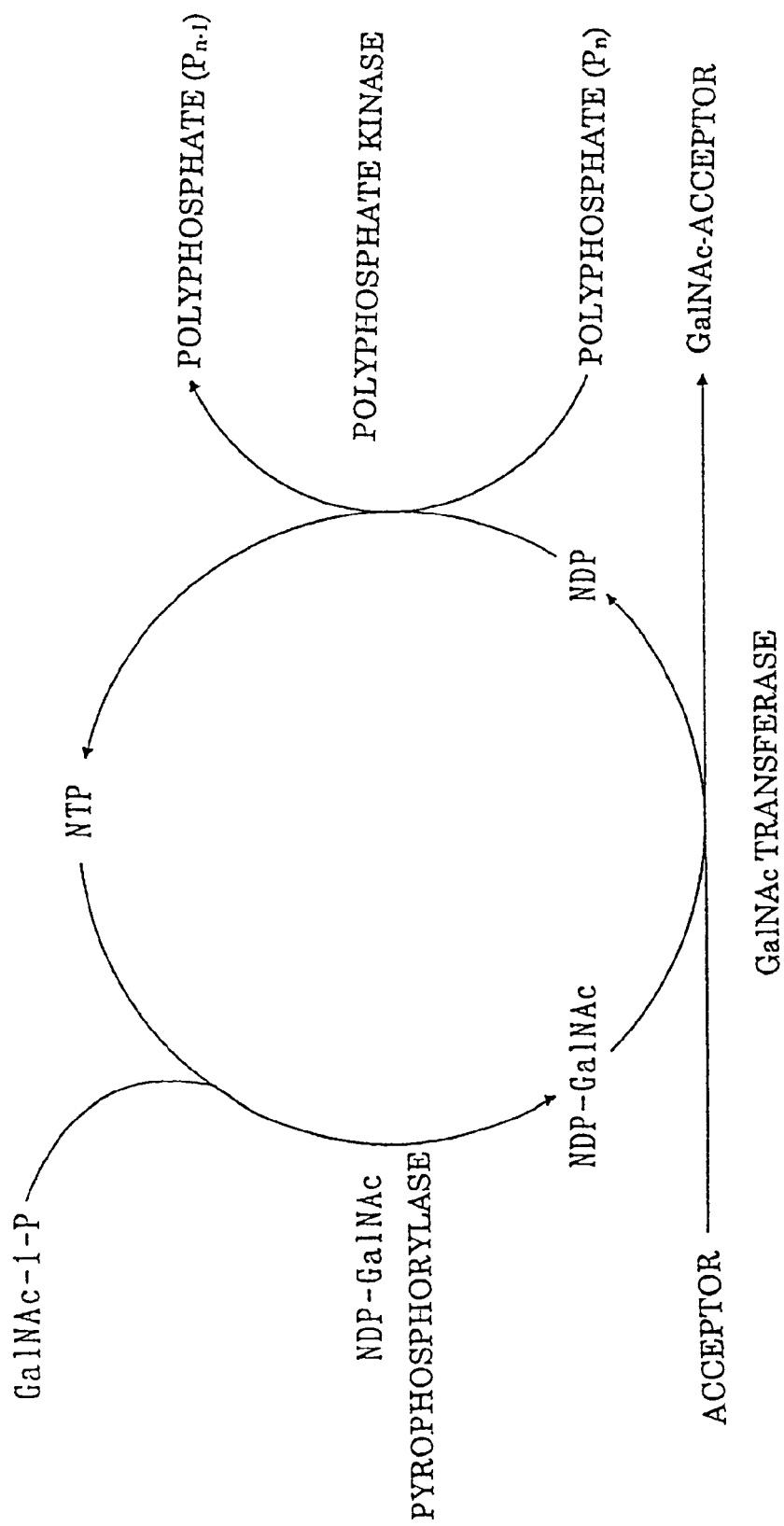
FIG. 9 shows the reaction scheme for the manufacture of an N-acetylgalactosaminylated compound of an acceptor sugar.

(7) A method for the manufacture of an N-acetylgalactosaminylated compound of an acceptor sugar, in which the N-acetylgalactosaminylated compound of an acceptor sugar is produced from a sugar nucleotide and the acceptor sugar by use of N-acetylgalactosaminyl transferase, and NDP formed in the reaction is transformed to NTP and then to a sugar nucleotide for recycling (FIG. 9).

The above-described synthesis systems described in (6) and (7) may simultaneously be conducted by causing NDP-GalNAc4-epimerase to react with NDP-GalNAc to form NDP-GlcNAc (FIGS. 8 and 9).

Figure 10:
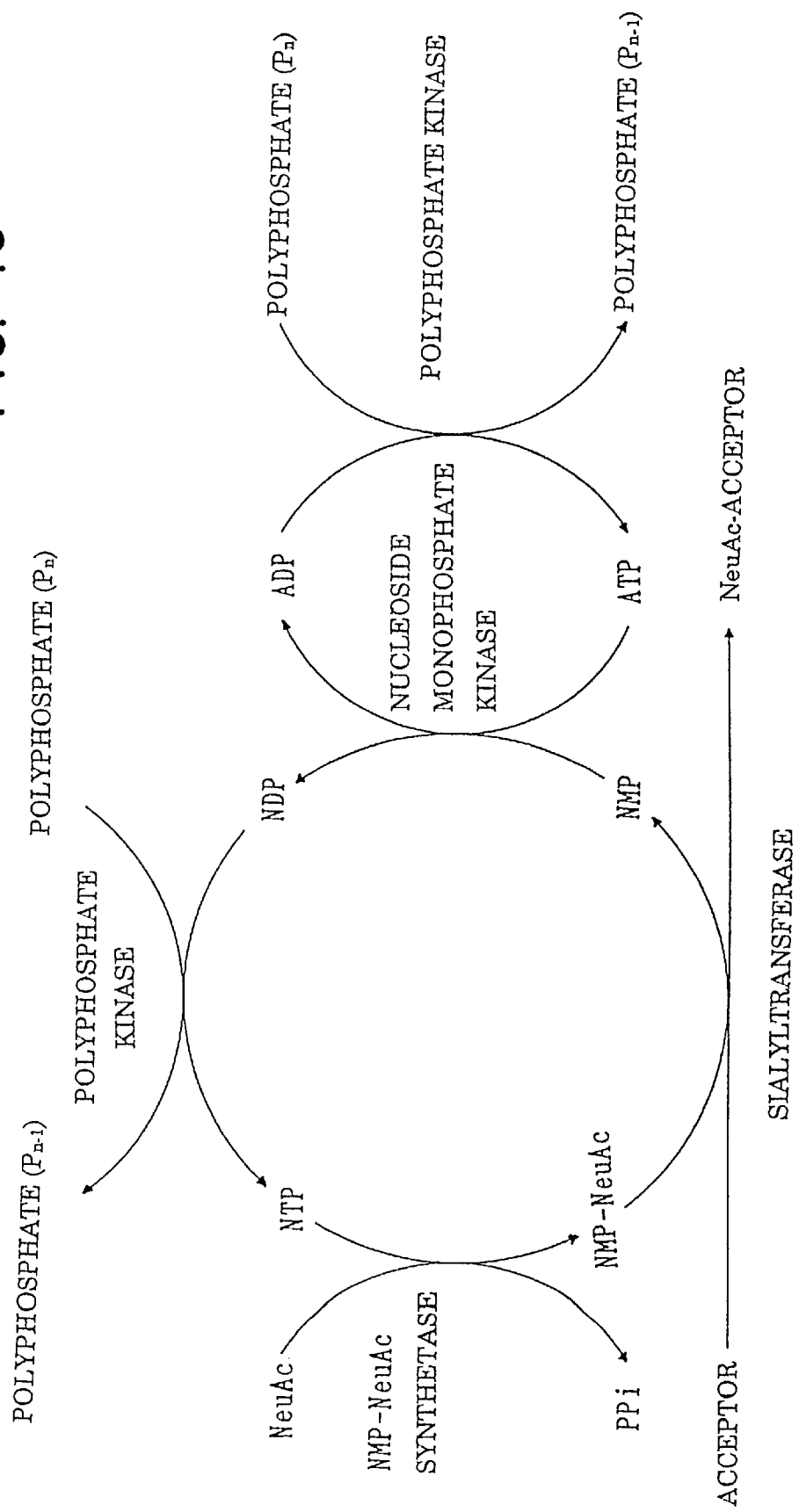
FIG. 10 shows the reaction scheme for the manufacture of a sialylated compound of an acceptor sugar.

(8) A method for the manufacture of a sialylated compound of an acceptor sugar, in which the sialylated compound of an acceptor sugar is produced from a sugar nucleotide and the acceptor sugar by use of sialyltransferase, and NMP formed in the reaction is transformed to NDP, then to NTP, and further to a sugar nucleotide for recycling (FIG. 10).

In the above-described synthesis system, the enzymes may be used in the form of cells of a microorganism, enzyme preparations, etc., similar to the case of the above-described polyphosphate kinase. The optimum reaction conditions of the above-described synthesis system may be determined within a known range in accordance with the final product; i.e., glycosylated product, by performing small-scale tests.

Specifically, the enzyme, such as NDP-sugar pyrophosphorylase, glycosyltransferase, or polyphosphate kinase, is used in an amount of 0.0001–100.0 units/ml, preferably 0.001–10.0 units/ml. The substrate, such as NTP, sugar 1-phosphate, an acceptor sugar, or polyphosphate, is used in an amount of 0.01–1,000 mM, preferably 1–200 mM. The synthesis reaction may be performed through addition of the enzyme(s) and the substrate(s) to an appropriate buffer having a pH of 3–10, and allowing the mixture to react at 30° C. or more (preferably 32–37° C.) for approximately 1–100 hour(s) with optional stirring.

The glycosylated product obtained from the above-described reaction may be separated and purified though a known method (a variety of column chromatographic methods).

EXAMPLES

The present invention will next be described in detail by way of examples, which should not be construed as limiting the invention thereto. Throughout the Examples, all procedures including preparation of DNA, digestion with restriction enzymes, ligation of DNA by T4 DNA ligase, and transformation of *Escherichia coli*, were performed in accordance with "Molecular Cloning" (edited by Maniatis et al., Cold Spring Harbor Laboratory, Cold Spring Harbor, N.Y. (1982)). Restriction enzymes, AmpliTaq DNA polymerase, and T4 DNA ligase were obtained from Takara Shuzo Co., Ltd. Nucleotides in reaction mixtures were determined by HPLC. Specifically, separation was carried out by use of an ODS-AQ312 column (YMC Co.) and a 0.5 M monopotassium phosphate solution as an eluent.

Example 1

Synthesis of NTP by Use of Polyphosphate Kinase (1) Cloning of a Gene of *Escherichia coli* Polyphosphate Kinase Chromosomal DNA of *Escherichia coli* K12 strain JM109 (obtained from Takara Shuzo Co.) was prepared by the method of Saito and Miura (*Biochim. Biophys. Acta.*, 72, 619(1963)). Using the obtained chromosomal DNA as a template, the following two primer DNAs were synthesized in accordance with a customary method and the *Escherichia coli* polyphosphate kinase (ppk) gene was amplified by PCR.

Primer (A): 5'-TACCATGGGTCAGGAAAAGCTATA-3' (SEQ ID NO:1)

Primer (B):
5'-ATGGATCCTTATTCAGGTTGTTCGAGTGA-3'
(SEQ ID NO:2)

PCR amplification of the ppk gene was performed by use of a DNA Thermal Cycler (Perkin-Elmer Cetus Instrument Co.) through 25 cycles of treatment, each cycle consisting of the steps of thermal denaturation (94° C., 1 minute), annealing (55° C., 1.5 minutes), and polymerization (72° C., 1.5 minutes), of a reaction mixture (100 μl) containing 50 mM potassium chloride, 10 mM Tris-hydrochloric acid (pH 8.3), 1.5 mM magnesium chloride, 0.001% gelatin, template DNA (0.1 μg), primer DNAs (A) and (B) (0.2 μM respectively), and AmpliTaq DNA polymerase (2.5 units).

After amplification of the gene, the reaction mixture was treated with a phenol/chloroform (1:1) mixture, and to an aqueous fraction was added ethanol in an amount twice the volume of the aqueous fraction to thereby precipitate DNA. The collected DNA precipitates were separated by agarose gel electrophoresis in accordance with the method of the literature ("Molecular Cloning," referred to above) to purify DNA fragments of 1.9 kb. The DNA was cleaved with restriction enzymes NcoI and BamHI and ligated with plasmid pTrc99A (obtained from Pharmacia Biotech. Co.)—which was digested with the same restriction enzymes NcoI and BamHI—using T4 DNA ligase. The *Escherichia coli* K12 strain JM109 was transformed by use of the ligation mixture, and plasmid pTrc-PPK was isolated from the obtained ampicillin-resistant transformant. The pTrc-PPK is a product obtained by inserting into pTrc99A, at the NcoI-BamHI cleavage sites downstream of the trc promoter, an NcoI-BamHI DNA fragment containing the *Escherlchia coli* ppk gene.

(2) Preparation of *Escherichia coli* polyphosphate kinase

*Escherichia coli* JM109 harboring plasmid pTrc-PKK was inoculated to a 2×YT culture medium (300 ml) containing 100 μg/ml of ampicillin and was then subjected to shaking culture at 37° C. When the culture reached 4×10$^8$ cells/ml, IPTG was added to the culture solution so that the final concentration thereof became 1 mM, and shaking culture was further carried out for five hours at 30° C. After termination of shaking culture, the cells were collected by centrifugal separation (9,000×g, 10 minutes) and then suspended in a buffer (60 ml) containing 50 mM Tris-hydrochloric acid (pH 7.5), 5 mM EDTA, 0.1% Triton X-100, and 0.2 mg/ml lysozyme. The suspension was maintained at 37° C. for one hour and then subjected to ultrasonic treatment so as to destroy the cells. The cellular residue was removed by additional centrifugation (20,000×g, 10 minutes).

The thus-obtained supernatant fraction was dialyzed against 50 mM Tris-hydrochloric acid (pH 7.8) containing 5 mM magnesium chloride and 1 mM 2-mercaptoethanol, so as to provide a crude enzyme sample, which had a polyphosphate kinase specific activity of 0.19 units/mg-protein. This value is about 1,000 times the specific activity (0.00018 units/mg-protein) of the reference bacterium (*Escherichia coli* JM109 harboring pTrc99A). Furthermore, the polyphosphate kinase was electrophoretically purified according to a method described by Akiyama et al. (*J. Biol. Chem.*, 267, 22556–22561 (1992)) to be homogeneous, to thereby obtain a purified enzyme sample. The specific activity of the purified enzyme sample was 0.7 units/mg-protein.

The polyphosphate kinase activity of the present invention was measured and the unit thereof was calculated using the following method.

An enzyme sample was added to 25 mM Tris-hydrochloric acid buffer (pH 7.8) containing 5 mM magnesium chloride, 100 mM ammonium sulfate, 5 mM ADP, and polyphosphate (in an amount equivalent to 150 mM inorganic phosphoric acid), and the mixture was maintained at 37° C. to undergo reaction. The reaction was terminated through thermal treatment at 100° C. for one minute. ATP in the reaction mixture was determined by high performance liquid chromatography (HPLC). The activity corresponding to formation of 1 μmol of ATP at 37° C. for one minute is defined as one unit.

(3) Synthesis (I) of NTP

A purified sample of polyphosphate kinase was added in an amount of 0.01 units/ml to 25 mM Tris-hydrochloric acid buffer (pH 7.8) containing 10 mM magnesium chloride, 100 mM ammonium sulfate, polyphosphate (in an amount equivalent to 50 mM inorganic phosphoric acid), and 5 mM NDP (ADP, CDP, GDP, UDP, IDP). The mixture was allowed to react at 37° C. for 18 hours. The results are shown in Table 1.

TABLE 1

|  | Product: NTP (mM) | |
| --- | --- | --- |
| Substrate: NDP (mM) | Polyphosphate-added | Polyphosphate-free |
| ADP (5.0) | ATP (1.01) | ATP (0) |
| CDP (5.0) | CTP (0.13) | CTP (0) |
| GDP (5.0) | GTP (0.19) | GTP (0) |
| UDP (5.0) | UTP (0.09) | UTP (0) |
| IDP (5.0) | ITP (0.76) | ITP (0) |

(4) Synthesis (II) of NTP

A crude polyphosphate kinase sample was added in an amount of 0.17 units/ml to 100 mM Tris-hydrochloric acid buffer (pH 7.8) containing 10 mM magnesium chloride, 100 mM ammonium sulfate, polyphosphate (in an amount equivalent to 50 mM inorganic phosphoric acid), and 25 mM NDP (ADP, CDP, GDP, UDP). The mixture was allowed to react at 37° C. for 16 hours. The results are shown in Table 2.

TABLE 2

| Substrate: NDP (mM) | Product: NTP (mM) |
| --- | --- |
| ADP (25.0) | ATP (12.2) |
| CDP (25.0) | CTP (5.63) |
| GDP (25.0) | GTP (10.8) |
| UDP (25.0) | UTP (12.3) |

(5) Activity of *Escherichia coli* Polyphosphate Kinase for Synthesis of Polyphosphate (NDP formation)

The activity for synthesis of polyphosphate from NTP as a substrate, which is the reverse of the reaction described in the Example, was analyzed using formation of NDP as an index. Briefly, a crude sample of polyphosphate kinase was added in an amount of 0.01 units/ml to 25 mM Tris-hydrochloric acid buffer (pH 7.8) containing 10 mM magnesium chloride, 100 mM ammonium sulfate, and 5 mM NTP (ATP, CTP, GTP, UTP), and the mixture was incubated at 37° C. for 18 hours.

The obtained mixture was analyzed through HPLC and the results are shown in Table 3. As is apparent from Table 3, no evidence for synthesis of polyphosphate from NTP substrates other than ATP was observed under the reaction conditions of the present invention.

TABLE 3

| Substrate: NTP (mM) | Product: NDP (mM) |
| --- | --- |
| ADP (5.0) | ADP (1.58) |
| CTP (5.0) | CDP (<0.01) |
| GTP (5.0) | GDP (<0.01) |
| UTP (5.0) | UDP (<0.01) |

Example 2

Synthesis of UDP-glucose (UDPG) from UDP by Use of Polyphosphate Kinase (1) Cloning of a Gene of *Escherichia coli* UDP-glucose Pyrophosphorylase Chromosomal DNA of *Escherichia coli* K12 strain JM109 (obtained from Takara Shuzo Co.) was prepared by the method of Saito and Miura (*Biochim. Biophys. Acta.*, 72, 619(1963)). Using the obtained chromosomal DNA as a template, the following two primer DNAs were synthesized in accordance with a customary method and the *Escherichia coli* UDP-glucose pyrophosphorylase (galU) gene (Weissborn et al., *J. Bacteriol.*, 176, 2661(1994)) was amplified by PCR.

Primer (C):
5'-GCGAATTCTGATATACTGGGATGCGATAC-3'
(SEQ ID NO:3)

Primer (D):
5'-ACGTCGACACCGATACGGATGTATCTT-3'
(SEQ ID NO:4)

PCR amplification of the galU gene was performed by use of a DNA Thermal Cycler (Perkin-Elmer Cetus Instrument Co.) through 25 cycles of treatment, each cycle consisting of the steps of thermal denaturation (94° C., 1 minute), annealing (55° C., 1.5 minutes), and polymerization (72° C., 1.5 minutes), of a reaction mixture (100 µl) containing 50 mM potassium chloride, 10 mM Tris-hydrochloric acid (pH 8.3), 1.5 mM magnesium chloride, 0.001% gelatin, template DNA (0.1 µg), primer DNAs (C) and (D) (0.2 µM respectively), and AmpliTaq DNA polymerase (2.5 units).

After amplification of the gene, the reaction mixture was treated with a phenol/chloroform (1:1) mixture, and to an aqueous fraction was added ethanol in an amount twice the volume of the aqueous fraction to thereby precipitate DNA. The collected DNA precipitates were separated by agarose gel electrophoresis in accordance with the method of the literature ("Molecular Cloning," referred to above) to purify DNA fragments of 1.0 kb. The DNA was cleaved with restriction enzymes EcoRI and SalI and ligated with plasmid pTrc99A (obtained from Pharmacia Biotech. Co.)—which was digested with the same restriction enzymes EcoRI and SalI—using T4 DNA ligase. The *Escherichia coli* K12 strain JM109 was transformed by use of the ligation mixture, and plasmid pTrc-galU was isolated from the obtained ampicillin-resistant transformant. The pTrc-galU is a product obtained by inserting into pTrc99A, at the EcoRI-SalI cleavage sites downstream of the trc promoter, an EcoRI-SalI DNA fragment containing the *Escherichia coli* galU gene.

(2) Preparation of *Escherichia coli* UDP-glucose Pyrophosphorylase

*Escherichia coli* JM109 harboring plasmid pTrc-galU was inoculated to a 2×YT culture medium (300 ml) containing 100 µg/ml of ampicillin and was then subjected to shaking culture at 37° C. When the culture reached 4×10$^8$ cells/ml, IPTG was added to the culture solution so that the final concentration thereof was 1 mM, and shaking culture was further carried out for 2.5 hours at 37° C. After cultivation, the cells were collected by centrifugal separation (9,000×g, 10 minutes) and then suspended in a buffer (60 ml) containing 50 mM Tris-hydrochloric acid (pH 7.5), 5 mM EDTA, 0.1% Triton X-100, and 0.2 mg/ml lysozyme. The suspension was maintained at 37° C. for one hour and then subjected to ultrasonic treatment so as to destroy the cells. The cellular residue was removed by additional centrifugation (20,000×g, 10 minutes). The thus-obtained supernatant fraction was provided as an enzyme sample. The UDP-glucose pyrophosphorylase activity of the enzyme sample is shown in the Table below together with that of the reference bacterium (*Escherichia coli* JM109 harboring pTrc99A).

TABLE 4

| Strain | UDP-glucose pyrophosphorylase activity |
| --- | --- |
| JM109/pTrc99A | <0.5 (units/mg-protein) |
| JM109/pTrc-galU | 20.4 |

The UDP-glucose pyrophosphorylase activity of the present invention was measured and the unit thereof was calculated using the following method.

An enzyme sample was added to 50 mM Tris-hydrochloric acid buffer (pH 8.0) containing 5 mM magnesium chloride, 6 mM UTP, and 6 mM glucose 1-phosphate, and the mixture was maintained at 37° C. to undergo reaction. The enzyme was inactivated by thermal treatment at 100° C. for five minutes. UDPG in the reaction mixture was determined by high performance liquid chromatography (HPLC). The activity corresponding to formation of 1 µmol of UDPG at 37° C. for one minute is defined as one unit.

(3) Synthesis UDPG

A sample of crude polyphosphate kinase and a sample of *Escherichia coli* UDP-glucose pyrophosphorylase were added in amounts of 0.17 units/ml and 2.0 units/ml respectively to 100 mM Tris-hydrochloric acid buffer (pH 7.6) containing 100 mM ammonium: sulfate, 10 mM magnesium chloride, 20 mM UDP, 30 mM glucose 1-phosphate, and polyphosphate (in an amount equivalent to 50 mM inorganic phosphoric acid), and the mixture was maintained at 37° C. UDPG present in the reaction mixture after the elapse of 7.5 hours was quantitatively determined by HPLC to confirm formation of 5.5 mM of UDPG. In the case in which the reaction time was 24 hours, formation of 10.1 mM of UDPG was confirmed. In a control comprising the above-described reaction mixture to which polyphosphate had not been added, UDPG was formed In an amount of 0.23 mM and 0.20 mM after the elapse of 7.5 hours and 24 hours, respectively.

Example 3

Synthesis of Oligosaccharide (1) Cloning of a Gene of *Escherichia coli* UDP-galactose 4-epimerase (galE)

Chromosomal DNA of *Escherichia coli* K12 strain JM109 (obtained from Takara Shuzo Co.) was prepared by the method of Saito and Miura (*Biochim. Biophys. Acta.*, 72, 619(1963)). Using the obtained chromosomal DNA as a template, the following two primer DNAs were synthesized in accordance with a customary method and the *Escherchia coli* UDP-galactose 4-epimerase (galE) gene was amplified by PCR.

Primer (E):
5'-TAGAATTCATACCATAAGCCTAATGGA-3'
(SEQ ID NO:5)

Primer (F):
    5'-TAGGATCCTTAATCGGGATATCCCTGT-3' (SEQ ID NO:6)

PCR amplification of the gale gene was performed by use of a DNA Thermal Cycler (Perkin-Elmer Cetus Instrument Co.) through 25 cycles of treatment, each cycle consisting of the steps of thermal denaturation (94° C., 1 minute), annealing (55° C., 1.5 minutes), and polymerization (72° C., 1.5 minutes) of a reaction mixture (100 μl) containing 50 mM potassium chloride, 10 mM Tris-hydrochloric acid (pH 8.3), 1.5 mM magnesium chloride, 0.001% gelatin, template DNA (0.1 μg), primer DNAs (E) and (F) (0.2 μM respectively), and AmpliTaq DNA polymerase (2.5 units).

After amplification of the gene, the reaction mixture was treated with a phenol/chloroform (1:1) mixture, and to an aqueous fraction there was added ethanol in an amount twice the volume of the aqueous fraction to thereby precipitate DNA. The collected DNA precipitates were separated by agarose gel electrophoresis in accordance with the method of the literature ("Molecular Cloning," referred to above) to purify DNA fragments of 1.0 kb. The DNA was cleaved with restriction enzymes EcoRI and DamHI and ligated with plasmid pTrc99A (obtained from Pharmacia Biotech. Co.)—which was digested with the same restriction enzymes EcoRI and BamHI sing T4 DNA ligase. The *Escherichia coli* K12 strain JM109 was transformed by use of the ligation mixture, and plasmid pTrc-galE was isolated from the obtained ampicillin-resistant transformant. The pTrc-galE is a product obtained by inserting into pTrc99A, at the EcoRI-BamHI sites downstream of the trc promoter, an EcoRI-BamHI DNA fragment containing the *Escherichia coli* galE gene.

(2) Preparation of *Escherichia coli* UDP-galactose 4-epimerase

*Escherichia coli* JM109 harboring plasmid pTrc-galE was inoculated to a 2×YT culture medium (300 ml) containing 100 μg/ml of ampicillin and was then subject ed to shaking culture at 37° C. When the culture reached 4×10$^8$ cells/ml, IPTG was added to the culture solution so that the final concentration thereof became 1 mM, and shaking culture was further carried out for five hours at 30° C. After cultivation, the cells were collected by centrifugal separation (9,000×g, 10 minutes) and then suspended in a buffer (60 ml) containing 50 mM Tris-hydrochloric acid (pH 7.5), 5 mM EDTA, and 0.2 mg/ml lysozyme. The suspension was maintained at 0° C. for 20 minutes and then subjected to ultrasonic treatment so as to destroy the cells. The cellular residue was removed by additional centrifugation (20,000×g, 10 minutes).

The thus-obtained supernatant fraction was used as a crude enzyme sample, which had a UDP-Gal 4-epimerase specific activity of 26.6 units/mg-protein. This value is about 2,400 times the specific activity (0.011 unit/mg-protein) of the reference bacterium (*Escherichia coli* JM109 harboring pTrc99A).

The UDP-galactose 4-epimerase activity of the present invention was measured and the unit thereof was calculated through use of the following method.

An enzyme sample was added to 40 mM Tris-hydrochloric acid buffer (pH 7.8) containing 10 mM UDP-glucose. The activity corresponding to formation of 1 μmol of UDP-galactose at 37° C. for one minute is defined as one unit.

Figure 11:
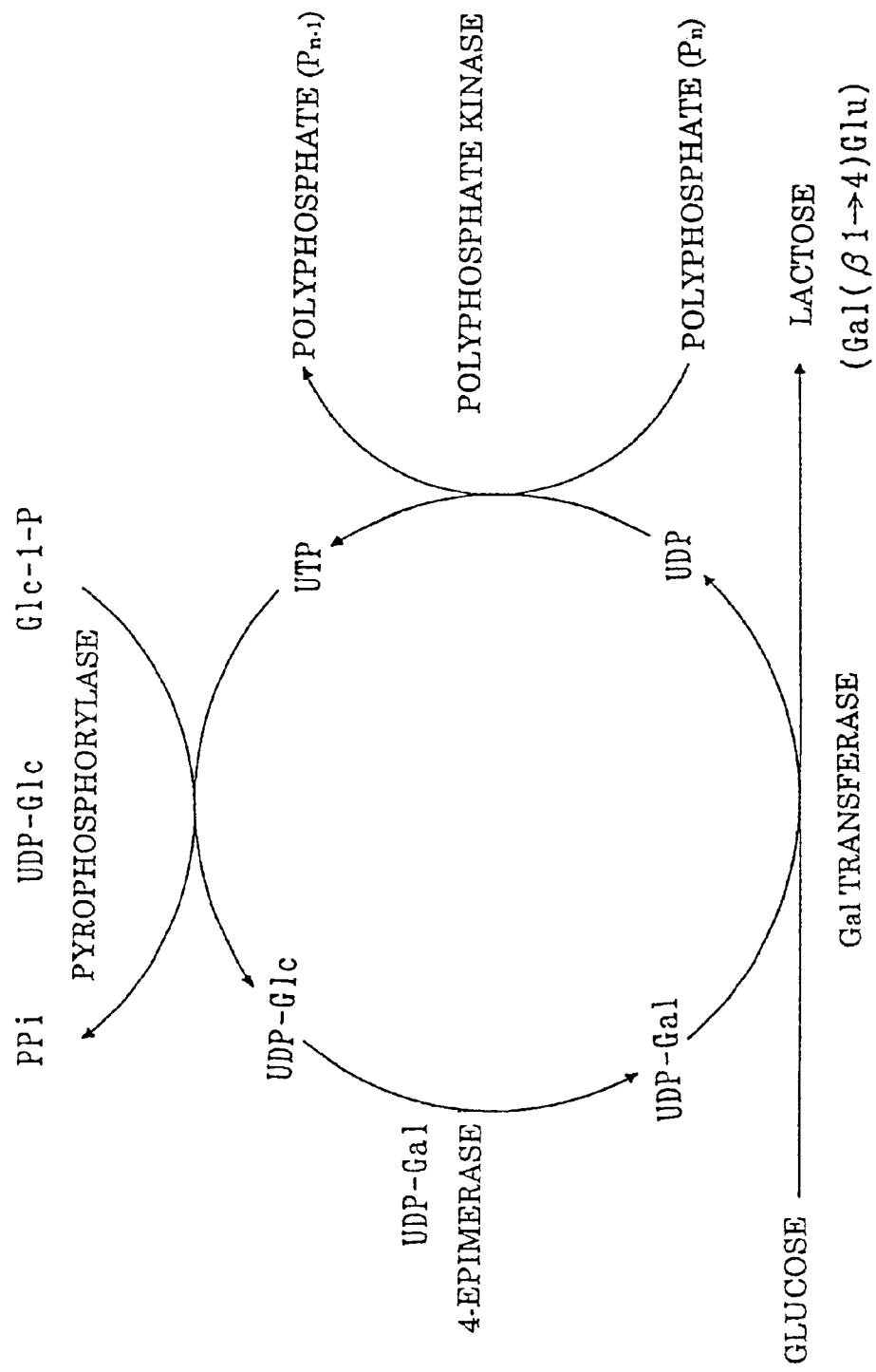
FIG. 11 shows the reaction scheme for the manufacture of lactose.

(3) Synthesis of lactose [Gal(β1-4)Glc] (see FIG. 11)

Polyphosphate was added to 25 mM Tris-hydrochloric acid buffer (pH 7.8) containing 10 mM magnesium chloride, 10 mM manganese chloride, 20 mM glucose, 4 mM UTP, 30 mM glucose 1-phosphate, and 0.2 mg/ml α-lactoalubumin, so that the concentration of phosphate became 150 mM. To the mixture were added 0.5 units/ml bovine milk-derived galactosyltransferase (obtained from Sigma Co.), 1.0 unit/ml UDP-galactose pyrophosphorylase, 1.0 unit/ml UDP-galactose 4-epimerase, and 0.1 units/ml polyphosphate kinase, and the resultant mixture was maintained at 37° C. for 20 hours. Formation of 12.4 mM lactose was confirmed through analysis of the reaction mixture by a sugar-analyzer (Dionex Co.).

Figure 12:
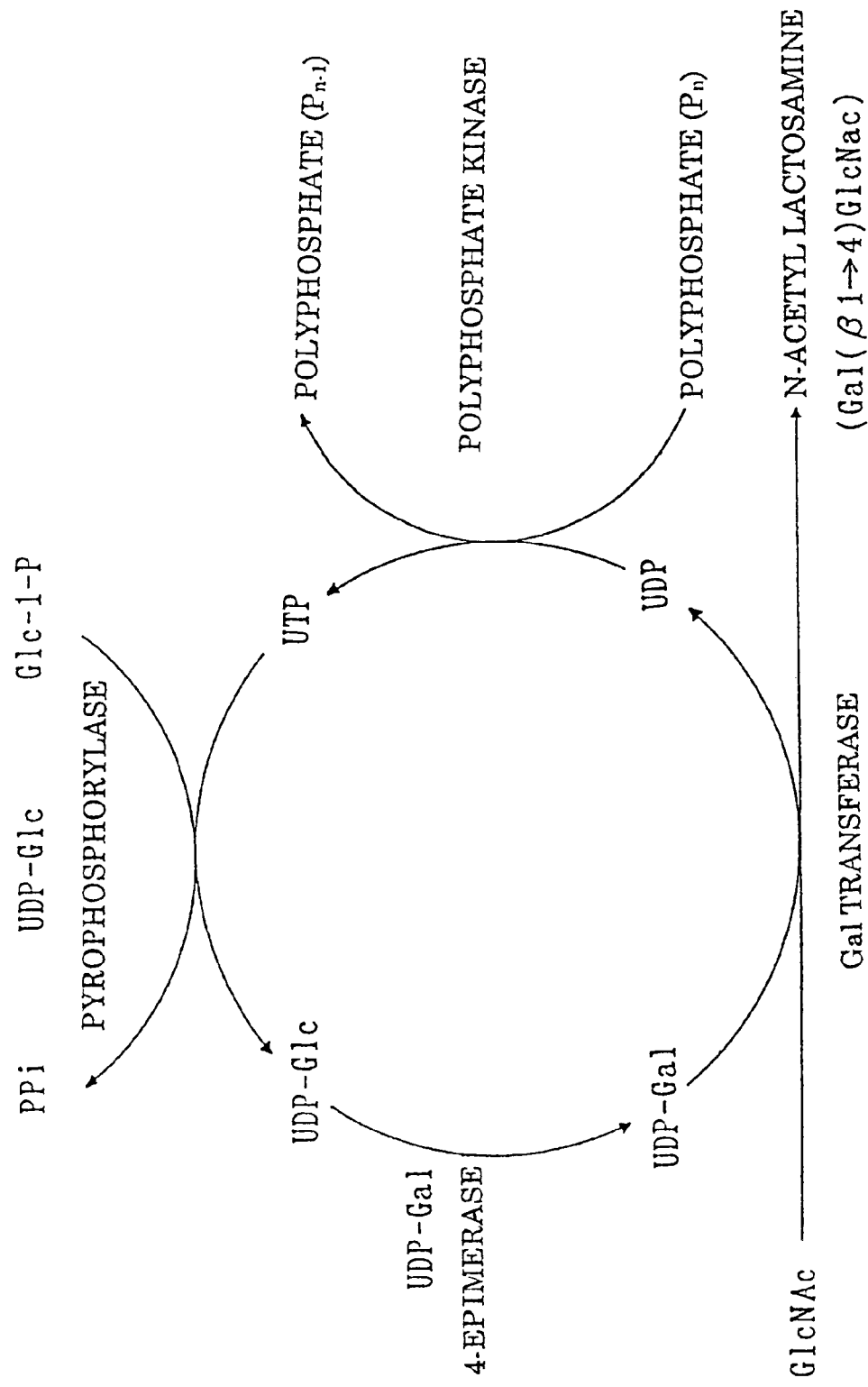
FIG. 12 shows the reaction scheme for the manufacture of N-acetyllactosamine.

(4) Synthesis of N-acetyllactosamine [Gal(β1-4)GlcNAc] (see FIG. 12)

Polyphosphate was added to 25 mM Tris-hydrochloric acid buffer (pH 7.8) containing 10 mM magnesium chloride, 10 mM manganese chloride, 20 mM N-acetylglucosamine, 4 mM UTP, and 30 mM glucose 1-phosphate, so that the concentration of phosphate became 150 mM. To the mixture were added 0.5 units/ml bovine milk-derived galactosyltransferase (obtained from Sigma Co.), 1.0 unit/ml UDP-galactose pyrophosphorylase, 1.0 unit/ml UDP-galactose 4-epimerase, and 0.1 units/ml polyphosphate kinase, and the resultant mixture was maintained at 37° C. for 20 hours. Formation of 13.6 mM of N-acetyllactosamine was confirmed through analysis of the reaction mixture by use of a sugar-analyzer (Dionex Co.).

As shown in the teachings above, the present invention provides a simple and low-cost enzymatic method of synthesizing NTP from NDP. Also, the invention allows low-cost recycle synthesis of sugar nucleotides and synthesis of, for example, oligosaccharides related thereto, while eliminating use of expensive phosphoenol pyruvate or ATP in a regeneration or transformation step from NDP to NTP in an enzyme-assisted synthesis system for oligosaccharides, which synthesis system is combined with a sugar nucleotide synthesis, etc.

It is claimed:

1. A process for producing a nucleoside 5'-triphosphate (NTP) from a nucleoside 5'-diphosphate (NDP) other than adenosine 5'-diphosphate (ADP), comprising reacting a polyphosphate kinase with NDP and a polyphosphate, said polyphosphate serving as a phosphate donor.

2. A process for regenerating a NTP from a NDP, other than ADP, that have been produced from another enzymatic process, comprising reacting a polyphosphate kinase with NDP produced from another enzymatic process and a polyphosphate, said polyphosphate serving as a phosphate donor.

3. A process for glycosylating an acceptor sugar, comprising reacting a glycosyltransferase with a sugar nucleotide and an acceptor sugar to form the glycosylated acceptor sugar, said sugar nucleotide being produced from NTP which is produced by reacting a polyphosphate kinase with a nucleoside 5'-monophosphate (NMP) or NDP produced from the glycosylation reaction and a polyphosphate, said polyphosphate serving as a phosphate donor.

4. A process for recycling a NMP or a NDP, other than ADP, that have been produced from an enzymatic reaction, to a NTP, comprising reacting a polyphosphate kinase with NMP or NDP produced from an enzymatic reaction and a polyphosphate, said polyphosphate serving as a phosphate donor.

5. The process according to claim 3, wherein the glycosyltransferase is galactosyltransferase, glucosyltransferase, fucosyltransferase, mannosyltransferase, glucuronyltransferase, sialyltransferase, N-acetylgalactosaminyltransferase, or N-acetylglucosaminyl transferase; and the glycosylated acceptor sugar is an acceptor sugar adduct with galactose, glucose, fucose, mannose, glucuronic acid, sialyic acid, N-acetylgalactosamine, or N-acetylglucosamine.

6. The process according to claim 3, wherein the sugar nucleotide is produced from NTP by reacting the NTP with NDP-glycosylpyrophosphorylase and sugar 1-phosphate, and optionally further with epimerase, dehydrogenase, or synthetase.

7. The process according to claim 5, wherein the sugar nucleotide is produced from NTP by reacting the NTP with NDP-glycosylpyrophosphorylase and sugar 1-phosphate, and optionally further with epimerase, dehydrogenase, or synthetase.

* * * * *

UNITED STATES PATENT AND TRADEMARK OFFICE
CERTIFICATE OF CORRECTION

PATENT NO. : 6,022,713
DATED : February 8, 2000
INVENTOR(S) : Toshitada NOGUCHI et al.

It is certified that error appears in the above-identified patent and that said Letters Patent is hereby corrected as shown below:

Drawings:
Figure 11, last line, change "Gal TRANSFERASE" to --Gal(β1-4)TRANSFERASE--;
last line, change "(Gal(β1-4)Glu)" to --(Gal(β1-4)Glc)--.

Figure 12, last line, change "Gal TRANSFERASE" to --Gal(β1-4)TRANSFERASE--;
last line, change "(Gal(β1-4)GlcNac)" to --(Gal(β1-4)GlcNAc)--.

Signed and Sealed this

Sixth Day of February, 2001

Attest:

*Attesting Officer*

Q. TODD DICKINSON
*Director of Patents and Trademarks*